(12) United States Patent
Jang et al.

(10) Patent No.: US 12,742,773 B2
(45) Date of Patent: Sep. 22, 2026

(54) COLORIMETRIC BIO SENSOR

(71) Applicant: QSTAG CO., LTD., Incheon (KR)

(72) Inventors: Jun Hyuck Jang, Suwon-si (KR); Dong Uk Kim, Ansan-si (KR); Eung Kyu Park, Incheon (KR); Dong Hoon Lee, Incheon (KR)

(73) Assignee: QSTAG CO., LTD., Incheon (KR)

( * ) Notice: Subject to any disclaimer, the term of this patent is extended or adjusted under 35 U.S.C. 154(b) by 650 days.

(21) Appl. No.: 18/332,120

(22) Filed: Jun. 9, 2023

(65) Prior Publication Data

US 2024/0019421 A1 Jan. 18, 2024

(30) Foreign Application Priority Data

Jul. 18, 2022 (KR) ........................ 10-2022-0087908

(51) Int. Cl.
*G01N 33/52* (2006.01)

(52) U.S. Cl.
CPC .................................. *G01N 33/526* (2013.01)

(58) Field of Classification Search
CPC ...... G01N 33/526; G01N 21/78; G01N 33/49; B01L 3/5023; B01L 2200/0631; B01L 2200/0652; B01L 2300/021
See application file for complete search history.

(56) References Cited

U.S. PATENT DOCUMENTS 4,912,034 A * 3/1990 Kalra ............... G01N 33/54366 435/805
5,658,747 A * 8/1997 Feldsine .......... G01N 33/56911 435/7.1
2003/0175153 A1* 9/2003 Anaokar .................. C12Q 1/60 422/68.1
2007/0031978 A1* 2/2007 Quinlan ............... G01N 33/521 436/514
2007/0244368 A1* 10/2007 Bayloff .................. A61B 10/02 600/300
2010/0311149 A1 12/2010 Bae et al.
2013/0236899 A1* 9/2013 Siciliano ............... B01L 3/5023 435/6.12

(Continued)

FOREIGN PATENT DOCUMENTS

JP 2002-243726 A 8/2002
KR 10-2009-0081764 A 7/2009

(Continued)

*Primary Examiner* — Melvin C. Mayes
*Assistant Examiner* — Sophia Y Lyle
(74) *Attorney, Agent, or Firm* — NSIP Law

(57) ABSTRACT

The colorimetric bio sensor includes: an upper housing including a blood cell separation module separating blood plasma from blood injected from the outside and spreads the separated blood plasma and a specimen delivery hole being located on the lower end of the blood cell separation module and formed to penetrate the upper housing, so that the lower end of the blood cell separation module is exposed to the outside; and a lower housing including a membrane containing a colorimetric reaction substance causing a colorimetric reaction with a target substance in the blood plasma by being in contact with the blood cell separation module through the specimen delivery hole, and a protrusion being located on the lower end of the membrane and protruding to a height corresponding to the depth of the specimen delivery hole.

10 Claims, 19 Drawing Sheets

(56) References Cited

U.S. PATENT DOCUMENTS

| | | | | |
|---|---|---|---|---|
| 2016/0125600 | A1 | 5/2016 | Lee et al. | |
| 2018/0071741 | A1* | 3/2018 | Kelly | G01N 35/00029 |
| 2022/0196560 | A1* | 6/2022 | Hatamian | G01N 21/8483 |

FOREIGN PATENT DOCUMENTS

| | | | | |
|---|---|---|---|---|
| KR | 10-2010-0130901 | A | 12/2010 | |
| KR | 10-2015-0009745 | A | 1/2015 | |
| KR | 10-1749627 | B1 | 12/2018 | |
| KR | 10-2021-0105025 | A | 8/2021 | |
| WO | WO-2005116651 | A2 * | 12/2005 | G01N 33/54388 |

* cited by examiner

【FIG.1】
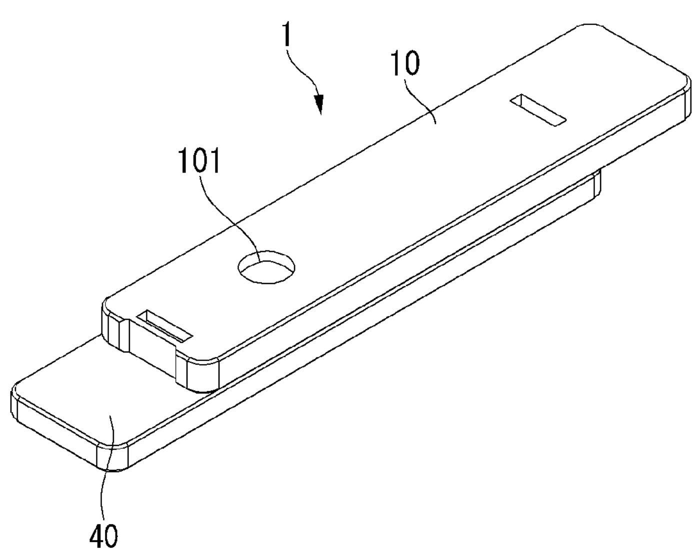

【FIG.2】
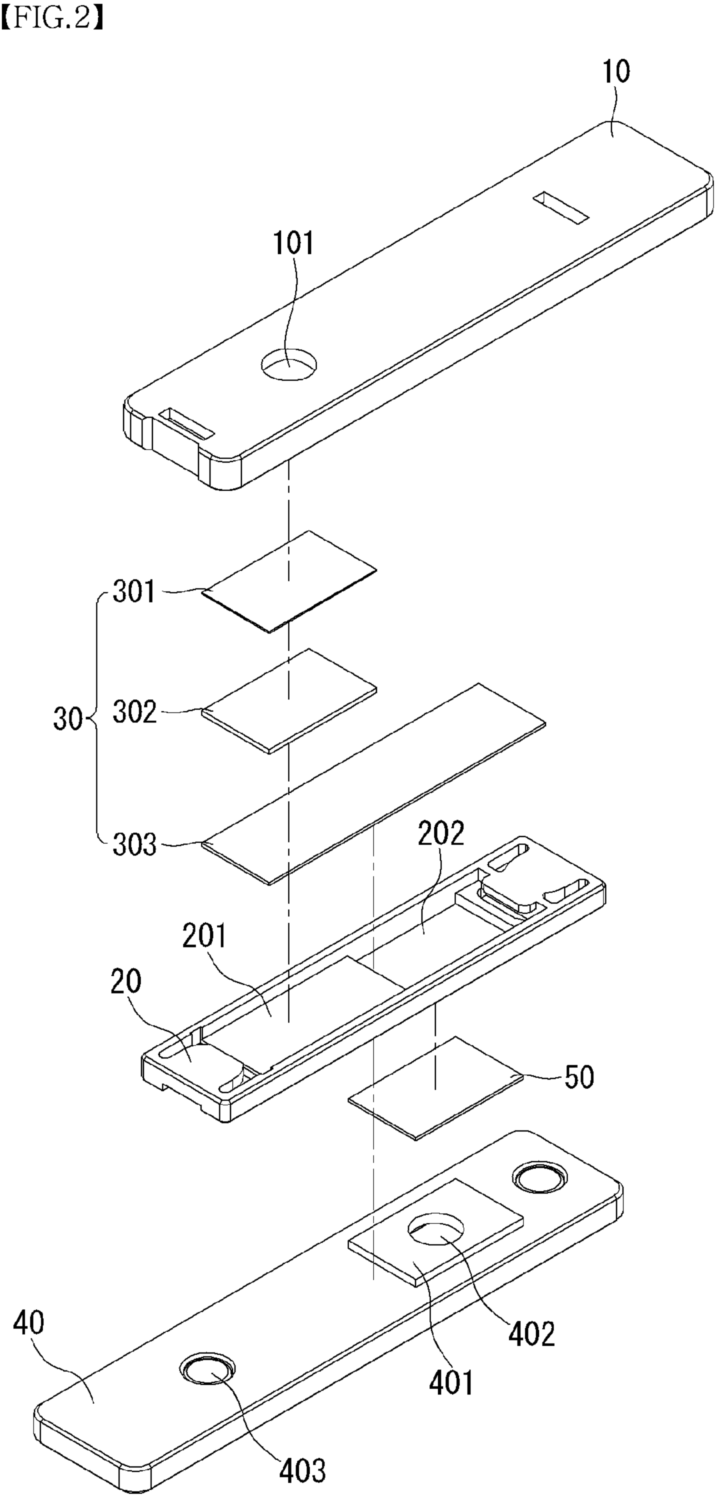

【FIG.3】
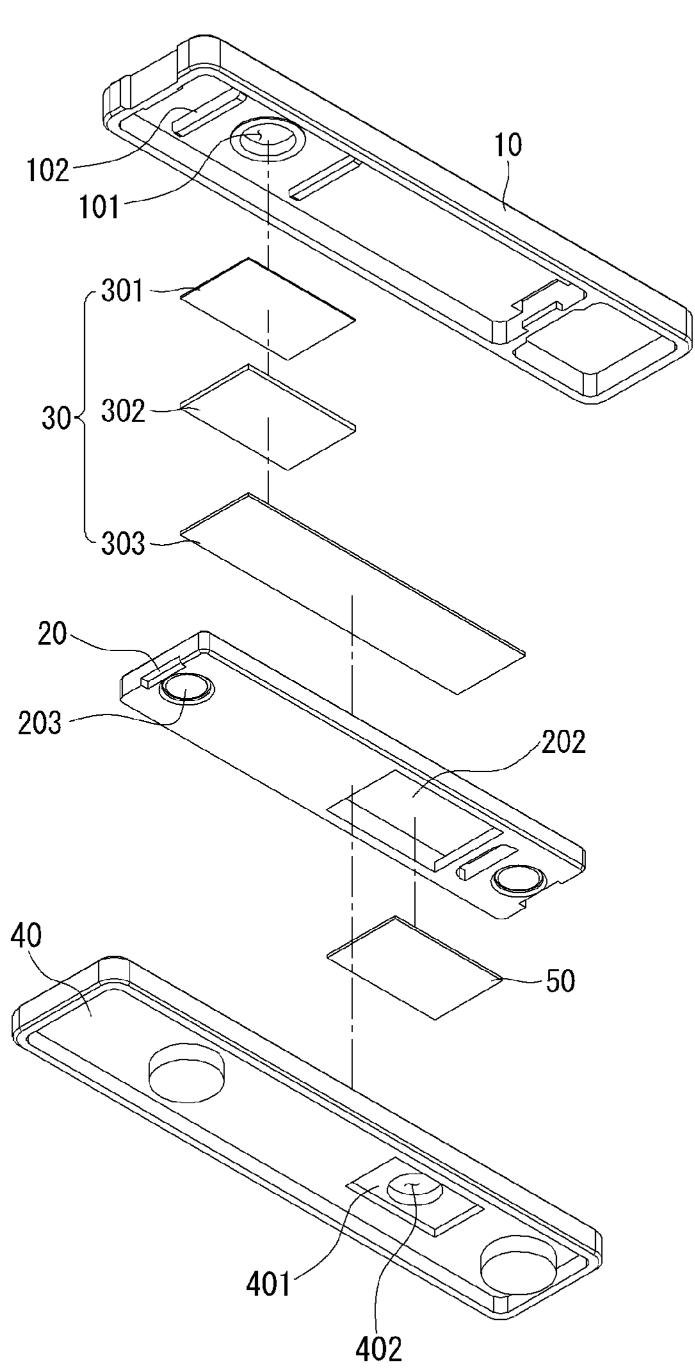

【FIG.4A】
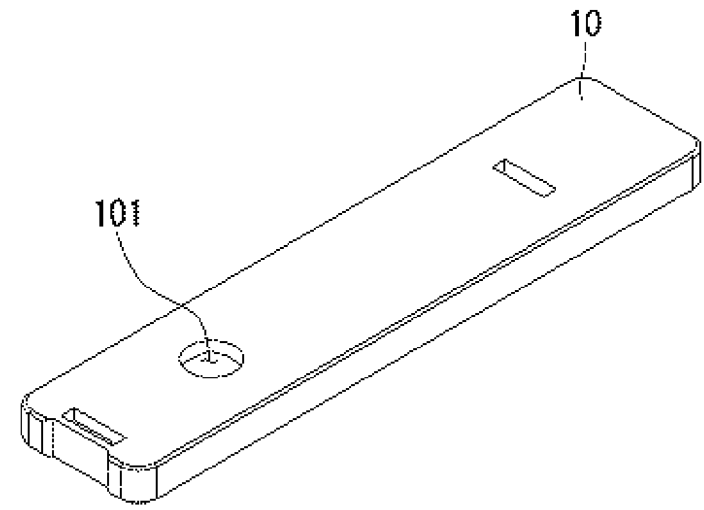
【FIG.4B】
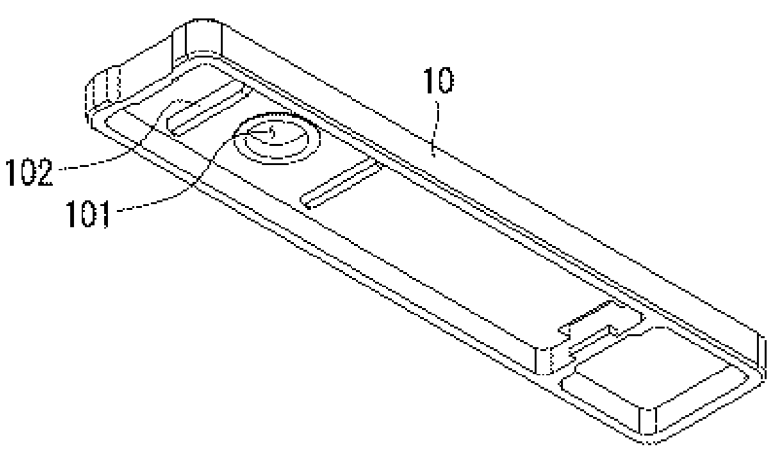

【FIG.5A】
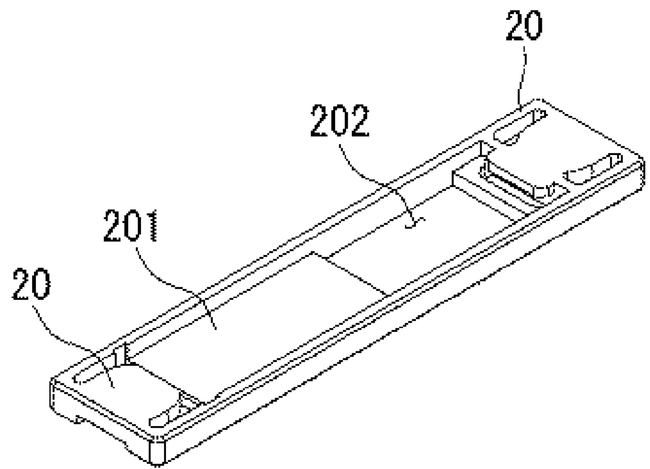
【FIG.5B】
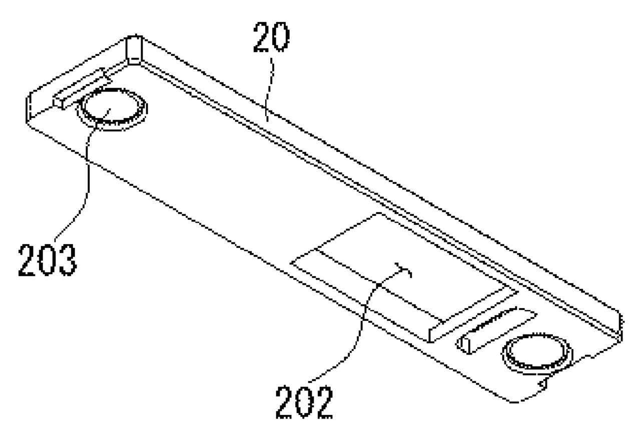

【FIG.6A】
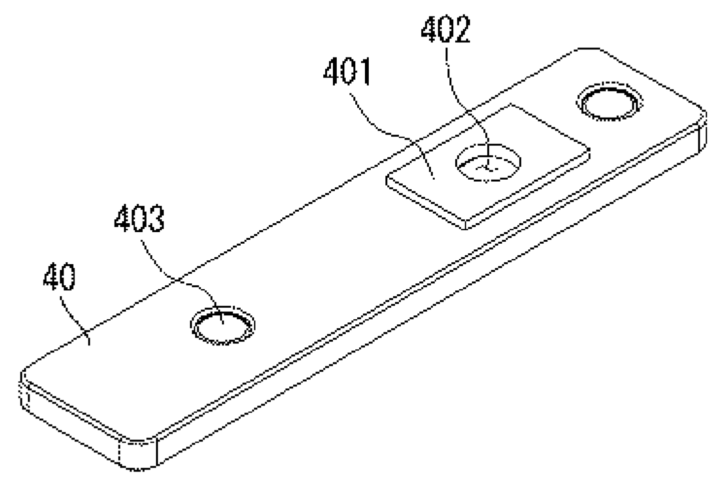
【FIG.6B】
40
401
402

【FIG.7】
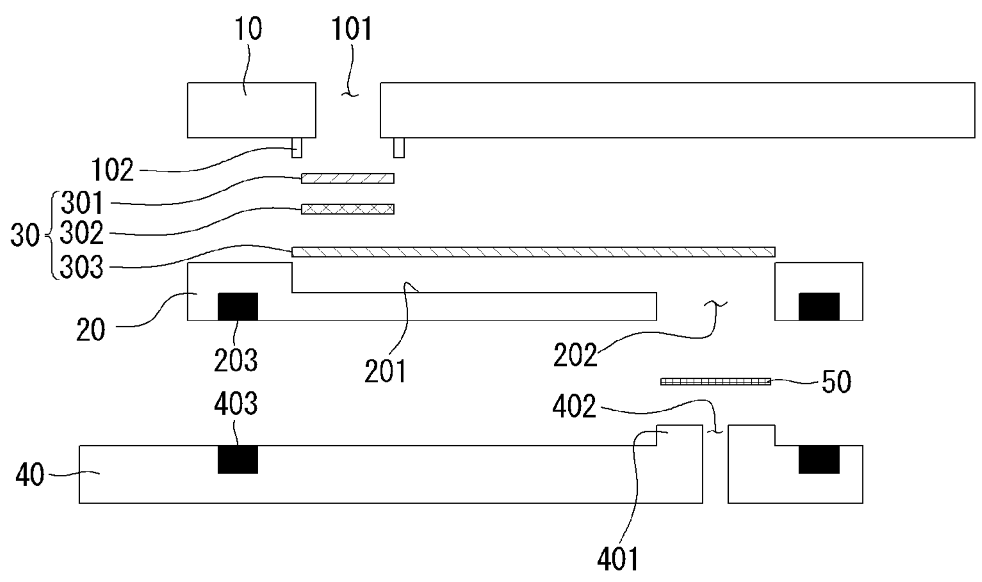

【FIG.8】
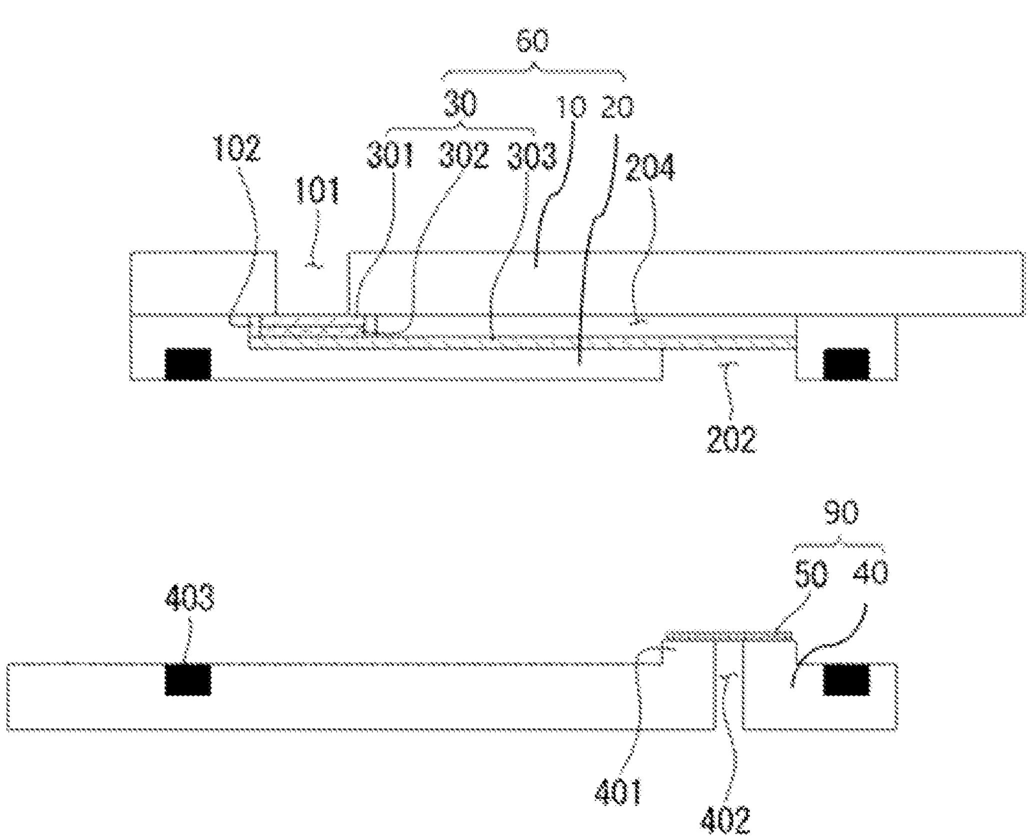

【FIG.9】
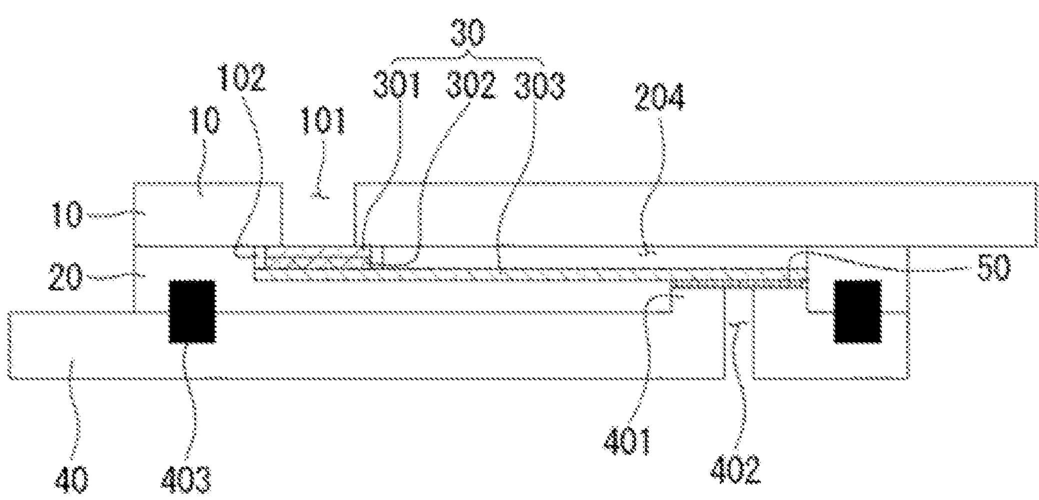

【FIG.10】
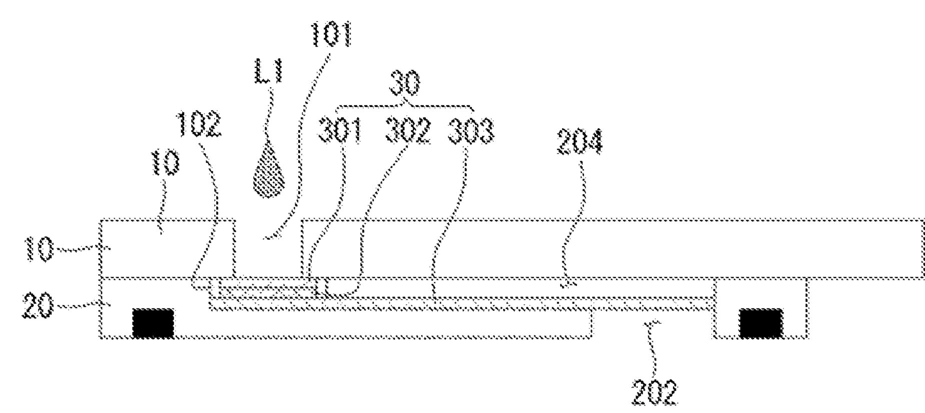
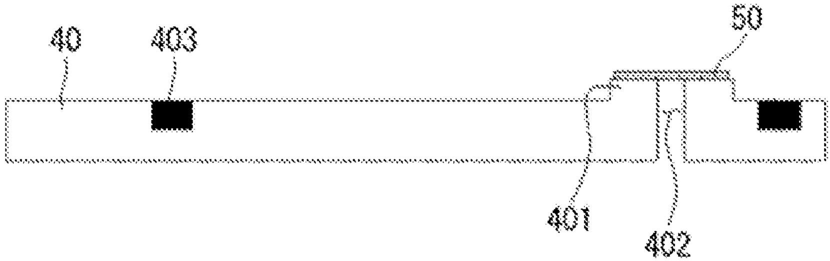

【FIG.11】
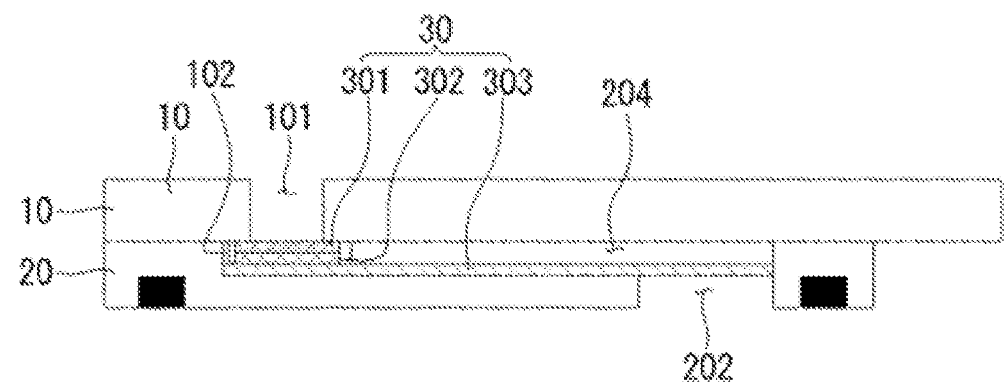

【FIG.12】
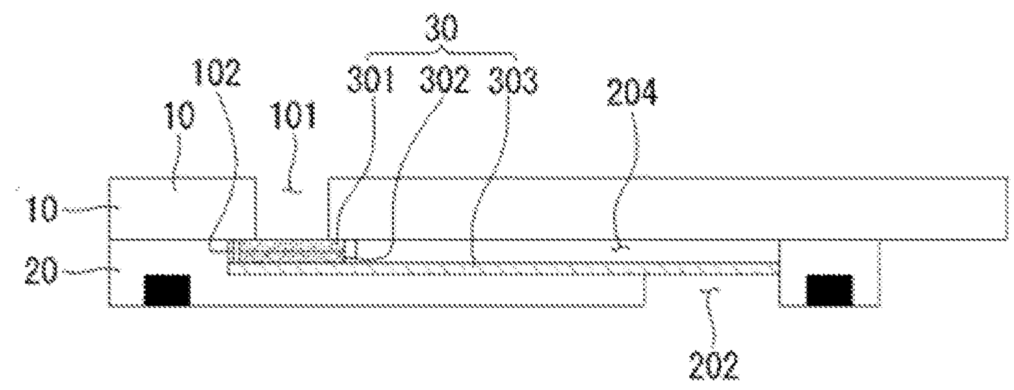
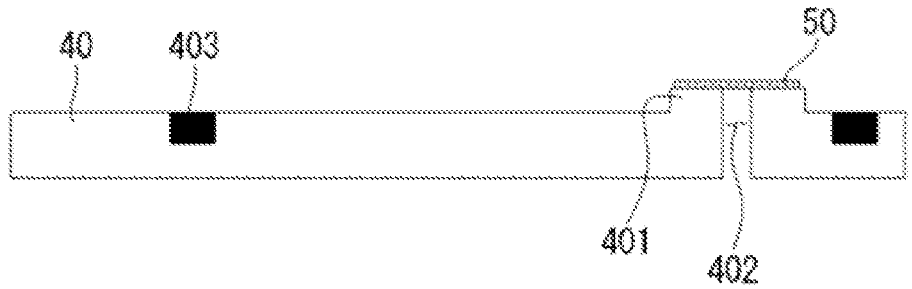

【FIG.13】
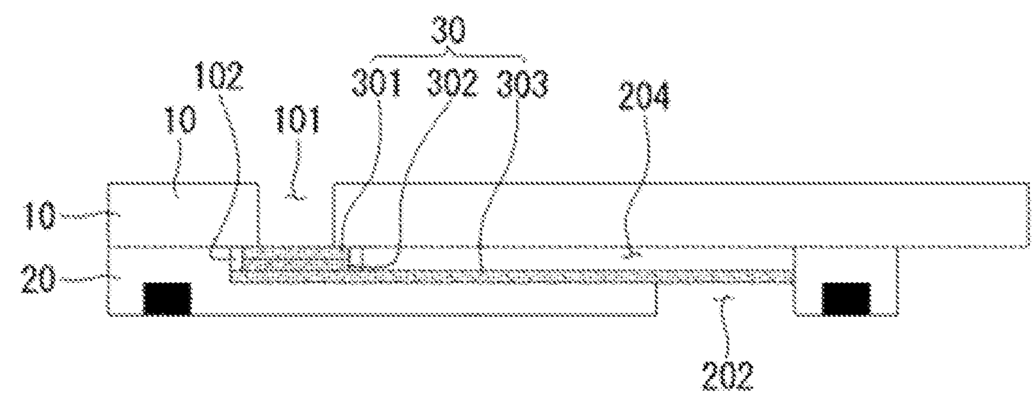

【FIG.14】
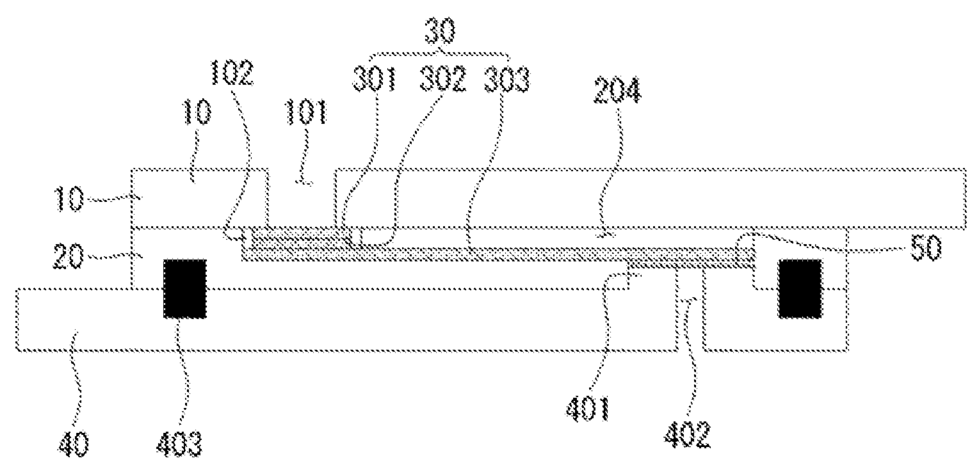

【FIG.15】
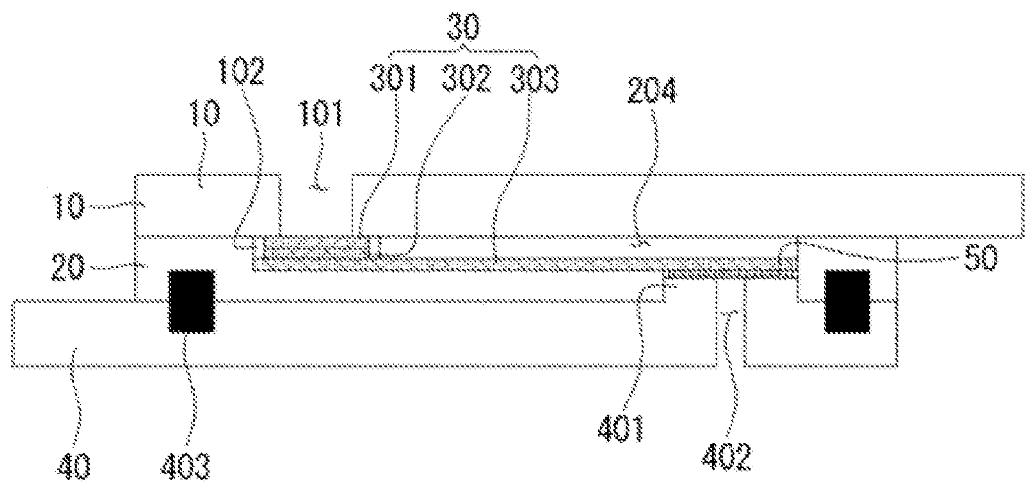

【FIG.16】
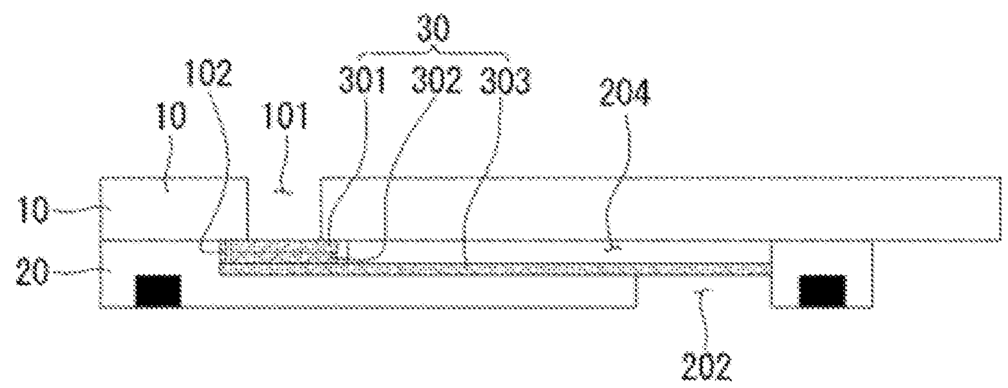
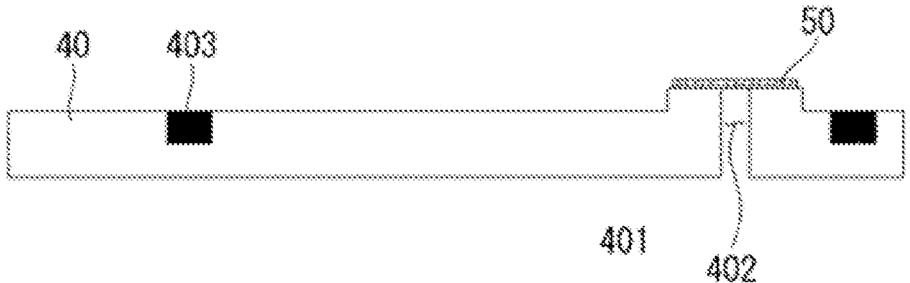

【FIG.17】
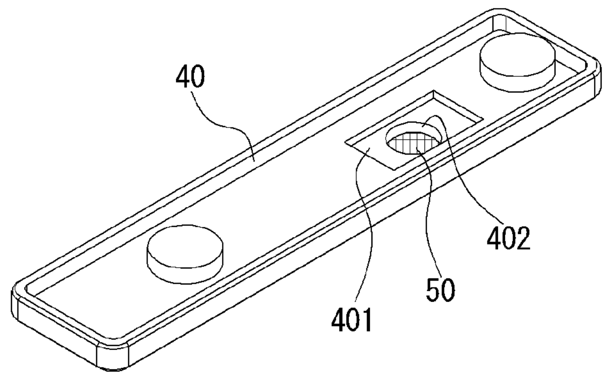

【FIG.18】
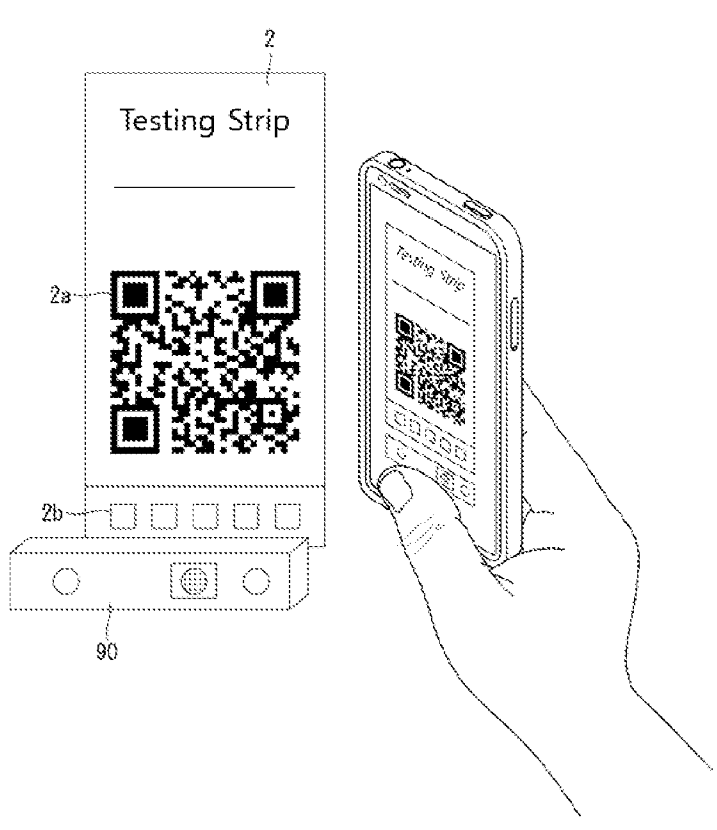

【FIG.19】
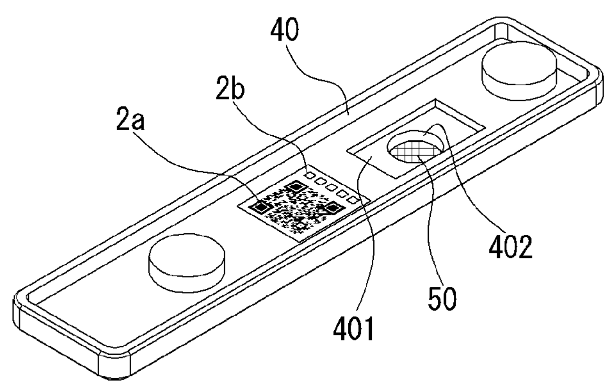

COLORIMETRIC BIO SENSOR

CROSS-REFERENCE TO RELATED APPLICATIONS

This application claims the priority benefit of Korean Patent Application No. 10-2022-0087908 filed on Jul. 18, 2022 in the Korean Intellectual Property Office, the disclosures of which are incorporated herein by reference.

BACKGROUND

1. Field

The present disclosure relates to a sensor capable of performing colorimetric measurement through blood separation and specimen reaction.

2. Description of the Related Art

A strip type bio sensor technology for detecting a target substance in a body fluid specimen such as blood of a body has been widely developed and used. The main purpose of the strip-type bio sensor is to check the presence or absence of a target substance in a body fluid and to diagnose various lesions therethrough.

Many bio sensors use a form in which a substance is detected by reacting blood plasma obtained by separating blood cells from blood. However, most of the structures of these bio sensors are such that blood cell separation and specimen reaction are performed in one structure, which may cause inconvenience in measurement. Additionally, there was a disadvantage in that sufficient and uniform blood plasma cannot be reacted because the reaction process is started before the sufficient amount of separated blood plasma is collected.

Therefore, there is a need for a bio sensor of a miniaturized strip structure which is capable of starting the reaction after collecting sufficient blood plasma, and of proceeding with various specimen reactions with only one blood injection, through the bio sensor structure in which the blood separation process and the specimen reaction process are separated.

DOCUMENT OF RELATED ART

Patent Document

Patent document 1: Korean Patent Application Publication No. 10-2015-0009745 ("BIO SENSOR CHIP", MiCo LTD., Jan. 27, 2015)

Patent document 2: Korean Patent Application Publication No. 10-2010-0130901("BIO SENSOR", OSANG HEALTHCARE CO., LTD., Dec. 14, 2010)

Patent document 3: Korean Patent No. 10-1933457("BIO SENSOR", BBB Inc., Dec. 21, 2018)

SUMMARY

It is possible to invent a sensor structure capable of separating a part of the sensor that proceeds with the blood cell separation process from a part of the sensor that proceeds with the reaction process of a specimen, and provide a sensor that can be used for colorimetric measurement by using the same.

An embodiment of a colorimetric bio sensor may include an upper housing including a blood cell separation module which separates blood plasma from blood injected from the outside and spreads the separated blood plasma, and a specimen delivery hole which is located on the lower end of the blood cell separation module and formed to penetrate the upper housing, so that the lower end of the blood cell separation module is exposed to the outside; and a lower housing including a membrane containing a colorimetric reaction substance capable of causing a colorimetric reaction with a target substance in the blood plasma by being in contact with the blood cell separation module through the specimen delivery hole, and a protrusion which is located on the lower end of the membrane, and protrudes to a height corresponding to the depth of the specimen delivery hole so as to press the membrane into contact with the blood cell separation module by being inserted into the specimen delivery hole.

Additionally, according to an embodiment, the upper housing may include at least one upper magnet located on the lower end of the upper housing, the lower housing may include a lower magnet located on the upper end of the lower housing to correspond to the upper magnet, and the lower housing may be coupled with the upper housing by the lower magnet and the upper magnet.

Additionally, according to an embodiment, the upper housing may further include a compression member at the upper portion of the specimen delivery hole.

Additionally, according to an embodiment, the compression member and the protrusion may include magnets.

Additionally, according to an embodiment, there may be a plurality of specimen delivery holes, there may be as many membranes and many protrusions as the number of the specimen delivery holes, and the number of kinds of the colorimetric reaction substances may correspond to the number of the specimen delivery holes.

Additionally, according to an embodiment, the blood cell separation module may include at least one mesh, at least one blood cell separation pad, and at least blood plasma spreading pad.

Additionally, according to an embodiment, in the blood cell separation module, the mesh may be located on the uppermost end, the blood cell separation pad for separating blood cells from a vertical blood flow may be located at the lower end of the mesh, and the blood plasma spreading pad for separating blood cells from a horizontal blood flow may be located at the lowermost end.

Additionally, according to an embodiment, the upper housing and the lower housing may be formed such that when being coupled to each other, one end of the upper housing and the other end of the lower housing protrude.

Additionally, according to an embodiment, the upper housing may include a guide part for fixing the blood cell separation module.

Additionally, according to an embodiment, the colorimetric bio sensor may further comprise a mesh between the blood cell separation module and the membrane.

Additionally, according to an embodiment, the lower housing may include a colorimetry check hole which is a through-hole formed in the center of the protrusion, so that the colorimetric reaction of the membrane can be indicated on the lower surface of the lower housing in a state where the lower housing is separated from the upper housing.

Additionally, according to an embodiment, the colorimetric bio sensor may further comprise a testing strip including a QR code and an RGB correction pad and disposed on the lower surface of the lower housing.

The colorimetric bio sensor of the blood separation strip structure of the present disclosure may proceed with a blood cell separation process in the upper housing and then proceed with a specimen reaction process with the coupled lower housing. Additionally, after the specimen reaction, the lower housing can be separated again and utilized for various colorimetric measurement methods.

BRIEF DESCRIPTION OF THE DRAWINGS

FIG. 1 is a perspective view of a colorimetric bio sensor of the present disclosure according to an embodiment.

FIG. 2 is an exploded top perspective view of the colorimetric bio sensor of FIG. 1.

FIG. 3 is an exploded bottom perspective view of the colorimetric bio sensor of FIG. 1.

FIG. 4A is a perspective view of an upper cover according to one embodiment.

FIG. 4B is a bottom perspective view of an upper cover according to one embodiment.

FIG. 5A is a perspective view of an upper base according to one embodiment.

FIG. 5B is a bottom perspective view of an upper base according to one embodiment.

FIG. 6A is a perspective view of a lower base according to one embodiment.

FIG. 6B is a bottom perspective view of a lower base according to one embodiment.

FIG. 7 is an exploded cross-sectional view of a colorimetric bio sensor according to an embodiment.

FIG. 8 is an exploded cross-sectional view in which an upper housing according to an embodiment is assembled.

FIG. 9 is a cross-sectional view of a colorimetric bio sensor according to an embodiment.

FIGS. 10 to 16 are operation diagrams showing an operation process of a colorimetric bio sensor according to an embodiment.

FIG. 17 is a bottom perspective view of a lower housing in which a specimen reaction has occurred.

FIG. 18 is a use state diagram illustrating a method of performing colorimetric measurement through an application by photographing a testing strip and a colorimetric bio sensor according to an embodiment.

FIG. 19 is a bottom perspective view of a lower housing including a testing strip according to an embodiment.

DETAILED DESCRIPTION

Advantages and characteristics of the present disclosure, and methods of achieving them will become apparent when the embodiments described below are considered in conjunction with the accompanying drawings. However, the present disclosure is not limited to the embodiments disclosed below, but will be implemented in a variety of different forms, and the present embodiments are only provided so that the description of the present disclosure is complete, and to fully inform those of ordinary skill in the art to which the present disclosure pertains of the scope of the disclosure, and the disclosure is defined only by the scope of the claims.

After briefly explaining the terms used in this specification, the present disclosure will be described in detail.

The terms used in the present disclosure have been selected from general terms that are currently used as widely as possible while considering the functions in the present disclosure, but they may vary depending on the intention of a person skilled in the art or precedent, the emergence of new technologies, or the like. In addition, in a specific case, there may also be a term arbitrarily selected by the applicant, and in this case, its meaning will be described in detail in the corresponding description of the disclosure. Therefore, the term used in the present disclosure should be defined based on not the simple name of the term, but the meaning of the term and the overall content of the present disclosure.

Throughout the specification, when a part "includes" or "comprises" a component, it means not that the part excludes other component, but instead that the part may further include other component unless expressly stated to the contrary. Also, the term, such as "part", "module", "unit", or the like, used in this specification refers to a unit for processing at least one function or operation, which may be embodied by software, hardware components such as FPGA or ASIC, or a combination of software and hardware. However, terms such as "part", "module", "unit", and the like are not meant to be limited to software or hardware. "Part", "module", "unit", or the like may be configured to be in an addressable storage medium, or configured to reproduce one or more processors. Thus, in an example, terms such as "unit", "module", "unit", or the like include components such as software components, object-oriented software components, class components and task components, processes, functions, properties, procedures, subroutines, segments of program code, drivers, firmware, microcode, circuits, data, databases, data structures, tables, arrays, and variables.

Hereinafter, embodiments of the present disclosure will be described in detail with reference to the accompanying drawings, so that those skilled in the art can easily carry out the present disclosure. And, in order to clearly explain the present disclosure, parts irrelevant to the description are omitted in the drawings. The terms including ordinal number such as, first, second, and the like may be used to explain various components, but the components should not be limited by these terms. Said terms are used in order only to distinguish one component from another component. For example, the first component can be designated as the second component without departing from the scope of the present disclosure, and, similarly, the second component can also be designated as the first component. The term "and/or" includes a combination of a plurality of related items or any one of the plurality of related items.

Hereinafter, the configuration of the colorimetric bio sensor 1 according to an embodiment of the present disclosure will be described in detail with reference to FIGS. 1 to 9, and an operation process of the colorimetric bio sensor 1 according to an embodiment of the present disclosure will be described with reference to FIGS. 10 to 19.

FIG. 1 is a perspective view of the colorimetric bio sensor 1 according to an embodiment of the present disclosure, FIGS. 2 and 3 are exploded perspective views of the colorimetric bio sensor 1 of FIG. 1, and FIGS. 4A to 6B are perspective views of each component of the colorimetric bio sensor 1.

An embodiment of the colorimetric bio sensor 1 will be described with reference to FIGS. 1 to 6B.

The colorimetric bio sensor 1 of the present disclosure may include a structure with which blood can be injected into the sensor, blood plasma can be extracted through the blood cell separation, and a colorimetric reaction can be generated in order to detect a target substance in the blood plasma, and its result can be checked by a colorimetric measurement scheme.

Referring to the exploded perspective view and bottom exploded perspective view of the colorimetric bio sensor 1 according to an embodiment of FIGS. 2 and 3, the colorimetric bio sensor 1 may include an upper housing 60 and a lower housing 90. Also, the upper housing 60 may include an upper cover 10, a blood cell separation module 30, and an upper base 20. Also, the lower housing 90 may include a lower base 40 and a membrane 50.

Specifically, the colorimetric bio sensor 1 of the present disclosure may include the upper cover 10 including a specimen injection hole 101 and a guide part 102; the upper base 20 which may be attached and located under the upper cover 10, and which may include an accommodation part 201 formed by engraving a recess in the inside and shaping a step to form an accommodating space 204, and a specimen delivery hole 202 that is spaced apart from the location of the specimen injection hole 101 of the upper cover 10; and the blood cell separation module 30 which includes at least one mesh 301, at least one blood cell separation pad 302, and at least one blood plasma spreading pad 303 located in an inner accommodation space 204 formed by assembling the upper cover 10 and the upper base 20. Additionally, the colorimetric bio sensor 1 may include the lower base 40 which includes a protrusion 401 located under the upper base 20 and embossed toward the upper surface by forming a step at the portion that comes into contact with the specimen delivery hole 202, and a colorimetry check hole 402 penetrating the upper and lower surfaces of the protrusion 401; and the membrane 50 located above the protrusion 401 of the lower base 40.

The upper housing 60, which is an upper structure of the colorimetric bio sensor 1, may be located on the upper portion of the lower housing 90. Also, the upper housing 60 may perform a blood cell separation process.

As shown in FIGS. 2 and 3, the upper housing 60 may be implemented in a rectangular parallelepiped shape having a rectangular cross-section with a horizontal length greater than a vertical length. The size and shape of the upper housing 60 are not limited to the illustration in the drawings, but any size and shape of the housing may be employed without limitation as long as it can contain a device for performing the blood separation process therein. In addition, the upper housing 60 may be formed so that its one end protrudes longer than the lower housing 90 when being combined with the lower housing 90. Through this, it is easy for a user to grip the colorimetric bio sensor 1, and to couple or separate the upper housing 60 with or from the lower housing 90.

The upper housing 60 may receive a specimen through the specimen injection hole 101, and separate blood cells passing through the blood cell separation module 30 in the accommodation space 204. Additionally, the upper housing 60 may deliver blood plasma obtained by separating blood cells to the membrane 50 of the lower housing 90 through the specimen delivery hole 202.

The upper housing 60 may include the upper cover 10 constituting the outer shape of the upper housing 60, the upper base 20, and the blood cell separation module 30 located inside the upper housing 60 to serve to separate the blood cells and deliver the blood plasma.

The upper cover 10 will be described with reference to FIGS. 4A and 4B.

The upper cover 10 may be located at the upper portion of the upper housing 60, and may form an outer shape of the upper housing 60 covering the blood cell separation module 30. When being coupled with the upper base 20, the upper cover 10 can form a space in which the blood cell separation module 30 can exist, and protect the blood cell separation device from external contaminants.

The upper cover 10 may include the specimen injection hole 101 through which a specimen is injected to be delivered to the blood cell separation module 30. In addition, the upper cover 10 may include the guide part 102 for fixing a blood cell separation device in the upper housing 60. Additionally, the upper cover 10 may include a compression member located on the upper portion of the specimen delivery hole 202 when assembled into the upper housing 60.

The specimen injection hole 101 may be included in the upper cover 10, and be formed to penetrate the upper and lower surfaces of the upper cover 10 so that a user can inject a specimen from the outside of the colorimetric bio sensor 1 onto the blood cell separation module 30 in the colorimetric bio sensor 1.

The specimen injection hole 101 may be present at one end of the upper cover 10 according to one embodiment. In addition, the specimen injection hole 101 may be formed with such a diameter that a specimen such as blood can be delivered to the blood cell separation module 30, and the mesh 301 and the pad(302, 303) of the blood cell separation module 30 can be fixed in the accommodation space 204 and receive the injected specimen.

The guide part 102 may be located around the specimen injection hole 101 on the lower surface of the upper cover 10, and may serve to fix the blood cell separation module 30 in the accommodation space 204. As shown in the drawing, the guide part 102 may be formed as partitions symmetrical with respect to the specimen injection hole 101 and arranged in parallel in a direction perpendicular to the longitudinal direction of the upper housing 60, so that they can fix the blood cell separation module 30. In addition to this, any shape of the guide part 102 may be employed without limitation as long as it has a shape corresponding to the shape of the blood cell separation module 30 and capable of fixing the blood cell separation module 30.

The compression member is located on the lower surface of the upper cover 10 to increase the compressive force at the point where the blood plasma spreading pad 303 and the membrane 50 come into contact when the upper housing 60 and the lower housing 90 are coupled, so that the blood plasma can be delivered to the membrane 50. Therefore, the compression member may be attached to a part of the upper cover 10 so as to be located at the top of the contact portion between the blood plasma spreading pad 303 and the membrane 50, or may not be attached, but be arranged in such a configuration that a guide fixes it.

Also, the compression member may include a material having magnetism in order to further improve compression capability. When the compression member include a material having magnetism, the compressive force between the blood plasma spreading pad 303 and the membrane 50 can be increased through attractive force with a material having magnetism of the protrusion 401 to be described later.

The upper base 20 will be described with reference to FIGS. 5A and 5B.

The upper base 20 may be located at the lower portion of the upper cover 10, and be coupled with the upper cover 10 to form the outer shape of the upper housing 60. In addition, the upper base 20 may be coupled with the upper cover 10 to form the accommodation space 204 capable of accommodating the blood cell separation module 30 therein.

The upper base 20 may include the accommodation part 201 in the form of forming a step on the top surface and engraving a recess in the inside, and the specimen delivery hole 202 located at one end of the accommodation part 201 and penetrating the upper and lower surfaces of the upper base 20 so that the membrane 50 and the blood plasma spreading pad 303 can come into contact with each other.

The upper base 20 may include at least one upper magnet 203 on its lower surface to be coupled to and separated from the lower housing 90.

The accommodation part 201 may be located on the upper surface of the upper base 20, and the step may be formed along the peripheral line of the accommodation part 201 of the upper base 20 in order to accommodate and fix the blood cell separation module 30 inside the upper housing 60. In addition, the accommodation part 201 may provide the accommodating space 204 capable of accommodating the blood cell separation module 30 inside the upper housing 60, by being combined with the upper cover 10.

In particular, the accommodation part 201 may be formed corresponding to the size of the blood plasma spreading pad 303 to accommodate and fix the blood plasma spreading pad 303 located at the lowermost end of the blood cell separation module 30. The blood cell separation module 30 may be fixed using the peripheral line of the accommodation part 201 as a guide.

The specimen delivery hole 202 may be included in the upper base 20, and be present at one end of the accommodation part 201. In this regard, the one end may be the opposite end to one end of the upper base 20 where the mesh 301 and the blood cell separation pad 302 are located, so that blood plasma can pass through the blood plasma spreading pad 303 for as long as possible.

The specimen delivery hole 202 may be formed in a shape penetrating the upper and lower surfaces of the upper base 20, so that the blood plasma spreading pad 303 and the membrane 50 can be brought into contact, and the blood plasma which has passed through the blood cell separation module 30 can be delivered to the membrane 50. In addition, the specimen delivery hole 202 may be formed to be larger than the size of the membrane 50, so that the membrane 50 of the lower housing 90 can come into contact with the blood plasma spreading pad 303.

At least one specimen delivery hole 202 may be included in the upper base 20. That is, two or more specimen delivery holes 202 may be included in the upper base 20, so that two or more membranes 50 can be brought into contact with one end of the blood plasma spreading pad 303. According to one embodiment, the specimen delivery hole 202 may be formed in the form of several long rectangles perpendicular to the longitudinal direction of the upper base 20 and penetrating the upper and lower surfaces thereof. Also, according to another embodiment, it may be formed in the form of several circular through-holes perpendicular to the longitudinal direction of the upper base 20.

The upper magnet 203 may be disposed on the lower surface of the upper base 20. In addition, the upper magnets 203 may be arranged to be fixed to the opposite ends of the lower surface of the base as shown in the drawing. Additionally, the upper magnet 203 may be located at a portion corresponding to the lower magnet 403 of the lower base 40 to be described later.

The upper magnet 203 may provide a coupling force to couple the upper housing 60 and the lower housing 90 when the upper housing 60 and the lower housing 90 are coupled to each other. Further, the upper magnet 203 may provide a pressure by being combined with the lower magnet 403, so that blood plasma can be delivered to the membrane 50 from the blood plasma spreading pad 303 to be described later.

The upper magnet 203 may be made of various materials having magnetism.

The blood cell separation module 30 may be located in the accommodation space 204 inside the upper housing 60 to separate blood cells from the injected blood and deliver the blood plasma to the membrane 50.

The blood cell separation module 30 may separate blood cells from the injected blood, and deliver the blood plasma to the membrane 50. The blood cell separation module 30 can separate blood cells by a vertical blood cell separation method in which blood cells are separated as blood moves in a vertical direction, and a lateral blood cell separation method in which blood cells are separated as blood moves in a horizontal direction. The blood cell separation module 30 may include at least one mesh 301, at least one blood cell separation pad 302, and at least one blood plasma spreading pad 303, respectively.

The mesh 301 may be included in the blood cell separation module 30, and be located in the accommodation space 204, and more specifically, be located under the specimen injection hole 101.

The mesh 301 can absorb blood injected through the specimen injection hole 101, and deliver the absorbed blood to the blood cell separation pad 302.

The mesh 301 may include a hydrophilic material to easily absorb blood. The mesh 301 may have a blood plasma collecting effect and a uniform blood plasma providing effect by including the hydrophilic material. The mesh 301 may be made of hydrophilic polyester, but the material of the mesh 301 is not limited to this, but may include any other materials, without limitation, that can collect and uniformly deliver blood.

In addition, two or more meshes 301 may be included in the blood cell separation module 30. The mesh 301 may be located between the specimen injection hole 101 and the blood cell separation pad 302, or may be located between the blood cell separation pad 302 and the blood plasma spreading pad 303, or may be located under the blood plasma spreading pad 303.

The mesh 301 may be formed to have a length corresponding to the length between the guide part (or partitions) 102 so as to be fixed by the guide part 102.

The blood cell separation pad 302 may be included in the blood cell separation module 30, and may be located in the accommodation space 204. Specifically, the blood cell separation pad 302 may be located just under the specimen injection hole 101, or may be located under the mesh 301 located under the specimen injection hole 101. Also, the blood cell separation pad 302 may be located on one end of the blood plasma spreading pad 303.

The blood cell separation pad 302 may directly absorb blood through the specimen injection hole 101, or may receive blood via the mesh 301. Additionally, the blood cell separation pad 302 may deliver the absorbed blood to the blood plasma spreading pad 303 or the mesh 301.

The blood cell separation pad 302 may separate blood cells from the absorbed blood. The blood cell separation pad 302 may separate blood cells during the delivery process of vertical flow through which it receives blood from the mesh 301 or specimen injection hole 101 located on the upper end, and delivers it to a second blood cell separation pad 302 or the mesh 301 located on the lower end.

The blood cell separation pad 302 may generally have a size similar to that of the mesh 301, and, similarly to the mesh 301, it may be formed to have a length corresponding to the length between the guide part (or partitions) 102 so as to be fixed by the guide part 102.

The blood cell separation pad 302 may be made of glass fiber. In addition, the blood cell separation pad 302 can be made of any other material, without limitation, as long as the material is suitable for separating blood cells from blood.

The blood plasma spreading pad 303 may be included in the blood cell separation module 30, and may be located in the accommodation space 204. Specifically, the blood plasma spreading pad 303 may be located on the lower end of the blood cell separation pad 302 and the mesh 301, and may be located in the accommodation part 201 of the upper base 20. In addition, the blood cell separation pad 302 and the mesh 301 may be located at the upper end of one end of the blood plasma spreading pad 303, and the specimen delivery hole 202 may be located at the lower end of the opposite end to the end where the blood cell separation pad 302 and the mesh 301 are located.

The blood plasma spreading pad 303 may be formed to correspond to the size of the accommodation part 201 of the upper base 20. The blood plasma spreading pad 303 may be formed to have such a size that it can be fixed by the peripheral line of the accommodation part 201 when being stacked on the accommodation part 201 according to the size of the accommodation part 201.

Like the blood cell separation pad 302, the blood plasma spreading pad 303 may be made of glass fiber or other material that can be used for the blood cell separation. The blood cell separation pad 302 and the blood plasma spreading pad 303 may be made of different materials.

The blood plasma spreading pad 303 may receive blood from the blood cell separation pad 302 and the mesh 301, and allow the blood to pass therethrough while delivering it to the membrane 50 or the mesh 301.

Also, the blood plasma spreading pad 303 can separate blood cells from the delivered blood. The blood plasma spreading pad 303 may receive blood from the mesh 301 and the blood cell separation pad 302 located at the upper end of one end, spread the blood in a horizontal direction, during which process the blood cells can be separated.

The blood plasma spreading pad 303 can deliver blood plasma to the mesh 301 or membrane 50 located on the lower end of the opposite end to the one end where the blood cell separation pad 302 is located through the processes of blood cell separation and blood plasma spreading.

Referring back to FIG. 2, the lower housing 90 will be described. The lower housing 90 may be located on and coupled to the lower portion of the upper housing 60 in the colorimetric bio sensor 1. The lower housing 90 may be formed to cause a colorimetric reaction by coupling the membrane 50 to the upper housing 60, and to observe or photograph through the colorimetry check hole 402, thereby enabling the colorimetric measurement.

The lower housing 90 may be formed such that it can be coupled with and separated from the upper housing 60. Accordingly, various colorimetric measurements can be performed by coupling and separating the lower housings 90 including the different membranes 50 with and from the upper housing 60 having the blood plasma obtained by separating blood cells from the blood injected one time therein.

The lower housing 90 may include the lower base 40 and the membrane 50.

The lower base 40 will be described with reference to FIGS. 6A and 6B.

The lower base 40 may be included in the lower housing 90 and form the outer shape of the lower housing 90, and may cause a colorimetric reaction by bringing the membrane 50 into contact with the blood plasma spreading pad 303 or the mesh 301 of the upper housing 60.

The lower base 40 may be made of acrylonitrile butadiene styrene (ABS). In addition to this material, any other material can be applied as a material for the lower base 40 without limitation if it can maintain its outer shape, has no problem in fixing each part included in the lower base 40 thereto, and is suitable for coupling with the upper housing 60.

The lower base 40 may be formed such that, when the upper housing 60 and the lower housing 90 are coupled to each other, the lower housing 90 protrudes at the opposite end of one end at which the upper housing 60 protrudes. With such structure, a user can easily grip the colorimetric bio sensor 1, and can easily separate and couple the upper housing 60 from and with the lower housing 90.

The lower base 40 may include the protrusion 401, the colorimetry check hole 402, and the lower magnet 403.

The protrusion 401 may be included in the lower base 40, and be located under the membrane 50. The protrusion 401 may be formed in a protruding shape, so that it has a step on a portion of the lower base 40. When the upper housing 60 and the lower housing 90 are coupled, the protrusion 401 may be located to correspond to the location of the specimen delivery hole 202.

The protrusion 401 may be formed to be inserted into the specimen delivery hole 202 when the upper housing 60 and the lower housing 90 are coupled for the specimen reaction. The protrusion 401 can bring the membrane 50 into contact with one end of the blood plasma spreading pad 303 located on the upper end of the specimen delivery hole 202 through the structure enabling the protrusion to be inserted into the specimen delivery hole 202.

The protrusion 401 may be formed to protrude longer than the depth of the specimen delivery hole 202, so that, when it is inserted into the specimen deliver port 202, it applies a pressure to the membrane 50 and the blood plasma spreading pad 303 with the protruding structure to easily deliver the blood plasma collected in the blood plasma spreading pad 303 to the membrane 50. The length of the protrusion 401 does not have to be longer than the depth of the specimen delivery hole 202, but it is sufficient as long as the protrusion can sufficiently press the membrane 50 and the blood plasma spreading pad 303 at the top of the protrusion 401.

In addition, the protrusion 401 may be formed in a size corresponding to the shape and diameter of the specimen delivery hole 202, so that, when the protrusion is inserted into the specimen delivery hole 202, the upper housing 60 and the lower housing 90 can be coupled and fixed to each other only by the coupling of the protrusion 401 and the specimen delivery hole 202.

Further, a plurality of protrusions 401 may be formed such that the corresponding number thereof matches the number of specimen delivery holes 202. According to an embodiment, when there are two or more specimen delivery holes 202, two or more protrusions 401 may be formed at positions respectively corresponding to the two or more specimen delivery holes 202 when the upper housing and the lower housing 90 are coupled to each other.

In the case where the compression member is present in the upper cover 10, the protrusion 401 can come into contact with the compression member when the upper housing 60 and the lower housing 90 are coupled to each other, so that it can compress the membrane 50 and the blood plasma spreading pad 303 with a stronger pressure. Through this, the protrusion 401 may allow the blood plasma to be more easily delivered from the blood plasma spreading pad 303 toward the membrane 50 than when there is no compression member.

The protrusion 401 may include a material having magnetism. Since the protrusion 401 includes a material with magnetism, it can compress the membrane 50 and the blood plasma spreading pad 303 with a stronger pressure in combination with the compression member having magnetism located at the upper portion of the specimen delivery hole 202. Through this, the protrusion 401 can move more blood plasma from the blood plasma spreading pad 303 to the membrane 50.

The colorimetry check hole 402 may be located in the protrusion 401, and exist in such a form that it penetrates the upper and lower surfaces of the lower base 40. Since the colorimetry check hole 402 exists penetrating the protrusion 401 located at the lower end of the membrane 50, the membrane 50 in which the colorimetric reaction has occurred can be checked when viewed from the bottom of the lower base 40.

The lower magnet 403 is included in the lower base 40, and at least one lower magnet may exist. The lower magnet 403 may be located at a portion of the lower base that is in contact with a portion of the upper base 20 where the upper magnet 203 exists when the lower housing 90 and the upper housing 60 are coupled to each other.

The lower magnet 403 may be made of a material having magnetism. Also, the lower magnet 403 may be made of a material which can cause the lower magnet to have an attractive force with the upper magnet 203.

When the upper housing 60 and the lower housing 90 are coupled to each other, the lower magnet 403 is coupled by attraction with the upper magnet 203, so that the protrusion 401 is located in the specimen delivery hole 202, and the housings are coupled and fixed together, applying a pressure to the membrane 50 and the blood plasma spreading pad 303 to enable the blood plasma to be well delivered. Besides, the lower magnet 403 can not only couple the upper housing 60 and the lower housing 90, but also facilitate their easy separation. The user can easily couple and separate the upper housing 60 with and from the lower housing 90 due to the presence of the upper magnet 203 and the lower magnet 403, and through this, it can be easy to proceed with the blood cell separation process and the specimen reaction process separately.

The membrane 50 may be located on the upper end of the protrusion 401, and the reaction of the specimen can proceed in the membrane. The membrane 50 may be stacked on the protrusion 401, and may be located to exist between the protrusion 401 and the blood plasma spreading pad 303 or the mesh 301 in contact with the blood plasma spreading pad 303 when the upper housing 60 and the lower housing 90 are coupled to each other.

The membrane 50 may include a substance capable of causing a colorimetric reaction with a target substance in a specimen. The reaction occurring between the substance included in the membrane 50 and the specimen can change the color of the membrane, which can be measured to determine whether the target substance is included in the specimen. Additionally, the membrane 50 may be made of a material such as polysulfone.

There may be two or more membranes 50. When there are two or more membranes 50, the membranes 50 may include different substances respectively to be capable of detecting different target substances. In addition, the membranes 50 may be respectively located on the two or more protrusions 401 to contact the blood plasma spreading pad 303.

Hereinafter, an assembly process of the colorimetric bio sensor 1 according to the first embodiment of the present disclosure will be described with reference to FIGS. 7 to 9.

FIG. 7 is a cross-sectional view showing a cross-section of each component of the colorimetric bio sensor 1 according to an embodiment.

According to the illustration of FIG. 7, the colorimetric bio sensor 1 may include the upper cover 10, the upper base 20, the membrane 50, the lower base 40, and the blood cell separation module 30 including the mesh 301 and the blood cell separation pad 302. The upper cover 10 may include the specimen injection hole 101 penetrating the upper and lower surfaces of the upper cover 10 at one end, and include the guide part 102 for fixing the mesh 301 and the blood cell separation pad 302, which is located on the lower surface of the upper cover 10 around the specimen injection hole 101.

According to the illustration of FIG. 7, the blood cell separation module 30 may be located at the lower portion of the upper cover 10. The blood cell separation module 30 may include at least one mesh 301, at least one blood cell separation pad 302, and at least one blood plasma spreading pad 303. The mesh 301 may be located at the lower end of the specimen injection hole 101 to receive and absorb blood through the specimen injection hole 101. Also, the blood cell separation pad 302 may similarly be located at the lower end of the mesh 301 to receive the blood from the mesh 301 and perform blood cell separation. The blood plasma spreading pad 303 may be located on the upper end of the accommodation part 201 of the upper base and on the lower end of the blood cell separation pad 302. The blood plasma spreading pad 303 may be formed to extend to the upper end of the specimen delivery hole 202, so that the blood plasma spreading pad can receive the blood from the blood cell separation pad 302 located on the upper end of one end of the blood plasma spreading pad, proceed with the blood cell separation process, and deliver the resultant to the membrane 50 to be located on the lower end of the opposite end to the one end.

According to the illustration of FIG. 7, the upper base 20 may be coupled with the upper cover 10 to form the accommodation space 204, and may include the accommodation part 201 which allows the blood cell separation module 30 to be located thereon. Additionally, the upper base 20 may include the specimen delivery hole 202 formed to penetrate the upper and lower surfaces of the upper base 20, so that the blood plasma spreading pad 303 and the membrane 50 can come into contact with each other, and may include at least one upper magnet 203 on the lower surface of the upper base 20 to facilitate the easy coupling and separation of the upper housing 60 and the lower housing 90.

According to the illustration of FIG. 7, the lower base 40 may include the protrusion 401 that can be located at the specimen delivery hole 202 when the upper housing 60 and the lower housing 90 are coupled, and may include at least one lower magnet 403 located at a portion of the upper surface of the lower base 40 which is in contact with the upper magnet 203. Additionally, the lower base 40 may include the colorimetric check hole 402 formed in such a form that the check hole penetrates the upper and lower surfaces of the protrusion 401 to check the specimen reaction of the membrane 50 from the lower surface.

According to the illustration of FIG. 7, the membrane 50 may be located on the upper end of the protrusion 401.

FIG. 8 is a cross-sectional view showing a cross section of the configuration of the upper housing 60 and the lower housing 90 according to an embodiment.

According to the illustration of FIG. 8, the upper housing 60 may be formed through the coupling of the upper cover 10, the blood cell separation module 30, and the upper base 20. The upper housing 60 may form the accommodation space 204 therein by the coupling of the upper cover 10 and the upper base 20, and may include the blood cell separation module 30 in the accommodation space 204. The mesh 301 and the blood cell separation pad 302 of the blood cell separation module 30 may be located at the lower end of the specimen injection hole 101, and may be fixed by the guide part 102 of the upper cover 10. Further, the blood plasma spreading pad 303 of the blood cell separation module 30 may be fixed by the accommodation part 201.

According to the illustration of FIG. 8, the lower housing 90 may be formed by the coupling of the lower base 40 and the membrane 50. The membrane 50 may be formed to cover one surface of the colorimetric check hole 402 by being located on upper end of the protrusion 401 of the lower base 40.

FIG. 9 is a cross-sectional view of the colorimetric bio sensor 1 formed by the coupling of the upper housing 60 and the lower housing 90 according to an embodiment.

According to the illustration of FIG. 9, the upper housing 60 and the lower housing 90 may be coupled to each other through at least one magnet present in each of them. In addition, the upper housing 60 and the lower housing 90 may be coupled to each other in a staggering manner, so that one end of the upper housing 60 protrudes and the other end of the lower housing 90 protrudes. Through this, the user can easily grip the colorimetric bio sensor 1, thereby enabling the easy coupling and separation thereof.

According to the illustration of FIG. 9, the colorimetric bio sensor 1 may be formed such that the protrusion 401 is inserted into the specimen delivery hole 202 through the coupling between the housings. Further, the colorimetric bio sensor 1 may bring the membrane 50 located on the upper end of the protrusion 401 into contact with the blood plasma spreading pad 303 through the coupling between the housings.

Hereinafter, the operation process of the colorimetric bio sensor 1 according to an embodiment of the present disclosure will be described with reference to FIGS. 10 to 19.

FIG. 10 is an operation diagram showing the injection of blood into the blood cell separation module 30 in the upper housing 60 through the specimen injection hole 101.

According to the embodiment of FIG. 10, the user may start the blood cell separation process by injecting the blood into the specimen injection hole 101 in a state where the upper housing 60 and the lower housing 90 are separated from each other.

FIG. 11 is an operation diagram showing that the mesh 301 absorbs the blood injected through the specimen injection hole 101.

According to the embodiment of FIG. 11, the mesh 301 can absorb the injected blood and deliver it to the blood cell separation pad 302. The mesh 301 may be made of a hydrophilic material to absorb a larger amount of blood.

FIG. 12 is an operation diagram showing that the blood cell separation pad 302 absorbs the blood delivered from the mesh 301.

According to the embodiment of FIG. 12, the blood cell separation pad 302 can receive and absorb the blood from the mesh 301 located on the upper end thereof, and separate blood cells from the blood. The blood cell separation pad 302 can proceed with the vertical-type blood cell separation process in the blood flow in the vertical direction.

FIG. 13 is an operational diagram showing that the blood plasma spreading pad 303 absorbs the blood delivered from the blood cell separation pad 302.

According to an embodiment of FIG. 13, the blood plasma spreading pad 303 can receive, from the blood cell separation pad 302 located on the upper end of one end of the blood plasma spreading pad, the blood from which blood cells have been first separated, and can proceed with the lateral-type blood cell separation process in a horizontal blood flow. The blood plasma spreading pad 303 moves the blood from one end to the opposite end and proceeds with a secondary blood cell separation process, thereby further enhancing the blood cell separation effect. The blood plasma spreading pad 303 can collect blood plasma, which is obtained by separating blood cells from the blood through the above processes, at the end of the blood plasma spreading pad 303.

FIGS. 14 and 15 are operational diagrams showing that the collected blood plasma is moved to the membrane 50 and the blood is absorbed by the membrane 50, through the coupling between the housings.

According to one embodiment of FIG. 14, a user can couple the upper housing and the lower housing 90 with the magnetic force of the upper magnet 203 and the lower magnet 403. The coupling can be made in such a form that the protrusion 401 of the lower housing 90 is inserted into the specimen delivery hole 202 of the upper housing 60, and through this, the membrane 50 located on the upper end of the protrusion 401 and one end of the second blood cell pad collecting the blood plasma can come into contact.

According to the embodiment of FIG. 15, the membrane 50 may receive and absorb, from one end of the blood plasma spreading pad 303, the blood plasma obtained by separating blood cells to cause the colorimetric reaction. The color of the membrane 50 may be changed due to the reaction, and this may be utilized for the colorimetric measurement.

FIG. 16 is an operation diagram showing that the lower housing 90 including the membrane 50 which has absorbed the blood plasma is separated and removed from the upper housing 60.

According to the embodiment of FIG. 16, a user can separate the lower housing 90 to measure the colorimetric value of the membrane 50 which has absorbed the blood plasma, and in which the specimen reaction has occurred.

FIG. 17 is a perspective view showing that the separated lower housing 90 is turned upside down.

According to the embodiment of FIG. 17, it is possible to check the membrane 50 in which the colorimetric reaction has occurred through the colorimetry check hole 402 of the lower housing 90 separated from the upper housing 60, even when the lower housing 90 is turned upside down. A user can utilize it for various colorimetric measurement methods.

FIGS. 18 and 19 are operation diagrams showing that colorimetric measurement is performed utilizing the lower housing 90 and a testing strip 2.

According to the embodiment of FIG. 18, the colorimetric bio sensor 1 may include the testing strip 2 including a QR code **2*a* and an RGB correction pad 2*b*. A method of checking through an application may be used after placing the lower housing 90 on the test strip 2, and photographing, through a mobile terminal or the like, the QR code 2*a*, the RGB correction pad 2*b*, and the lower housing 90 exposing the membrane 50 in which the colorimetric reaction has occurred through the colorimetry check hole 402**, together.

According to an embodiment of FIG. 19, the testing strip 2 including the QR code **2*a* of the colorimetric bio sensor 1 and the RGB correction pad 2*b* may be included by being printed or attached on the rear surface of the lower housing 90. A user can use a test method of checking through an application by photographing the lower surface of the lower housing 90 on which the testing strip 2** is printed.

Through the above-described methods, the user can self-diagnose various lesions by a colorimetric measurement scheme through blood.

While the embodiments of the present disclosure have been described above with reference to the accompanying drawings, those of ordinary skill in the art to which the present disclosure pertains will appreciate that the present disclosure may be implemented in other specific forms without changing the technical idea or essential features thereof. Accordingly, it should be understood that the embodiments described above are illustrative in all respects and not restrictive.

REFERENCE SIGN LIST

1: Colorimetric bio sensor
2: Testing strip
**2*a***: QR code
**2*b***: RGB correction pad
10: Upper cover
20: Upper base
30: Blood cell separation module
40: Lower base
50: Membrane
60: Upper housing
90: Lower housing
101: Specimen injection hole
102: Guide part
201: Accommodation part
202: Specimen delivery hole
203: Upper magnet
204: Accommodation space
301: Mesh
302: Blood cell separation pad
303: Blood plasma spreading pad
401: Protrusion
402: Colorimetric check hole
403: Lower magnet

What is claimed is:

1. A colorimetric bio sensor comprising:

an upper housing including a blood cell separation module which separates blood plasma from blood injected from the outside and spreads the separated blood plasma, and a specimen delivery hole which is located on the lower end of the blood cell separation module and formed to penetrate the upper housing, so that the lower end of the blood cell separation module is exposed to the outside; and a lower housing including a membrane containing a colorimetric reaction substance capable of causing a colorimetric reaction with a target substance in the blood plasma by being in contact with the blood cell separation module through the specimen delivery hole such that fluid communication is established therebetween, and a protrusion located on the lower end of the membrane, wherein the protrusion is formed to protrude to a height corresponding to a depth of the specimen delivery hole such that, when the protrusion is inserted into the specimen delivery hole, the protrusion presses the membrane positioned on an upper end of the protrusion into contact with the blood cell separation module, wherein the upper housing further includes a compression member at the upper portion of the specimen delivery hole, and wherein the compression member and the protrusion include magnets, such that when the upper housing and the lower housing are coupled, the blood cell separation module is compressed by a magnetic force via the magnets.

2. The colorimetric bio sensor of claim 1, wherein the upper housing includes at least one upper magnet located on the lower end of the upper housing, wherein the lower housing includes a lower magnet located on the upper end of the lower housing to correspond to the upper magnet, and wherein the lower housing is coupled with the upper housing by the lower magnet and the upper magnet.

3. The colorimetric bio sensor of claim 2, wherein the upper housing and the lower housing are formed such that when being coupled to each other, one end of the upper housing and the other end of the lower housing protrude.

4. The colorimetric bio sensor of claim 2, wherein the lower housing includes a colorimetry check hole which is a through-hole formed in the center of the protrusion, so that the colorimetric reaction of the membrane can be indicated on the lower surface of the lower housing in a state where the lower housing is separated from the upper housing.

5. The colorimetric bio sensor of claim 4, further comprising a testing strip including a QR code and an RGB correction pad and disposed on the lower surface of the lower housing.

6. The colorimetric bio sensor of claim 1, wherein the specimen delivery hole includes a plurality of specimen delivery holes, wherein a plurality of the membranes and a plurality of the protrusions are provided in numbers corresponding to a number of the plurality of specimen delivery holes, respectively, and wherein the colorimetric reaction substance includes a plurality of colorimetric reaction substances and each of the plurality of membranes includes a different colorimetric reaction substance, respectively, such that a number of the plurality of colorimetric reaction substances corresponds to the number of the plurality of specimen delivery holes.

7. The colorimetric bio sensor of claim 1, wherein the blood cell separation module includes at least one mesh, at least one blood cell separation pad, and at least blood plasma spreading pad.

8. The colorimetric bio sensor of claim 7, wherein in the blood cell separation module, the at least one blood cell separation pad separates blood cells from a vertical blood flow and is located at the lower end of the at least one mesh, and the at least one blood plasma spreading pad secondarily separates the blood cells from a horizontal blood flow and is located at the lower end of the at least one blood cell separation pad.

9. The colorimetric bio sensor of claim 1, wherein the upper housing includes a guide part for fixing the blood cell separation module.

10. The colorimetric bio sensor of claim 1, further comprising a mesh between the blood cell separation module and the membrane such that the membrane is indirectly in contact with the blood cell separation module via the mesh.

* * * * *